April 25, 1967 J. F. LINK, JR Plant Pat. 2,733
AZALEA
Filed Nov. 24, 1965 2 Sheets-Sheet 1
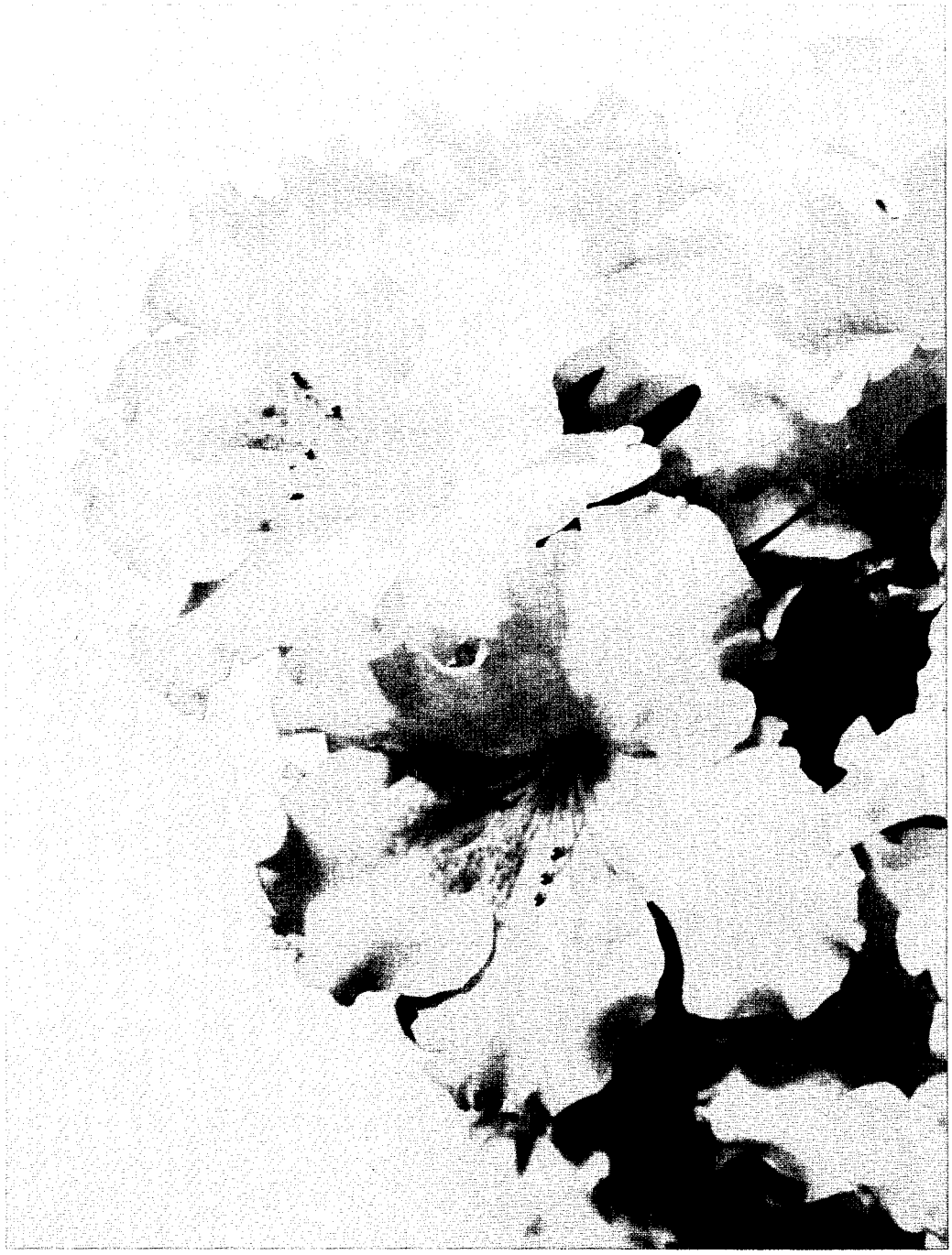
INVENTOR
JOHN F. LINK, JR.
BY Arthur Robert
HIS ATTORNEY April 25, 1967 J. F. LINK, JR Plant Pat. 2,733
AZALEA
Filed Nov. 24, 1965 2 Sheets-Sheet 2
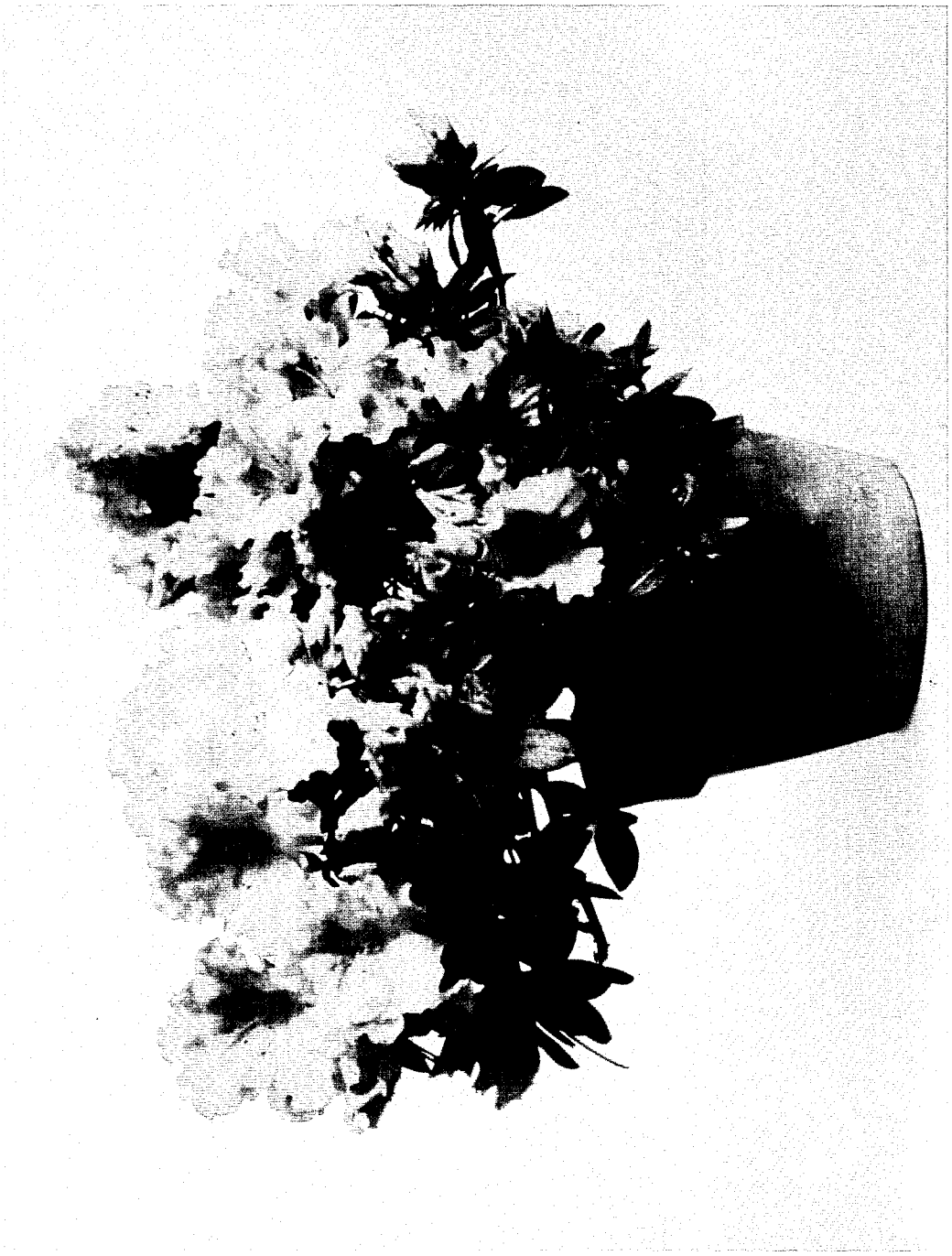
INVENTOR
JOHN F. LINK, JR.
BY Arthur J. Robert
HIS ATTORNEY United States Patent Office Plant Pat. 2,733
Patented Apr. 25, 1967

2,733
AZALEA

John F. Link, Jr., 3235 Cross Bill Road,
Louisville, Ky. 40213

Filed Nov. 24, 1965, Ser. No. 509,654
1 Claim. (Cl. Plt.—57)

(I) The present invention relates to a new and distinct variety of azalea plant of the Kurume class which I originated by crossing the Kurume azalea Hexe with the red seedling #1960–1 single, not patented, red Kurume, the 2nd being the seed parent and the other the pollen plant. The red seedling used as the cross was itself a cross between Hahn's Red of the Kurume variety and the Chimes of the Belgian Indica, this latter cross originating with J. W. Vestal, Jr. of Little Rock, Ark.

(II) As a result of this breeding, I have provided a new and distinct variety of azalea of the florist-forcing type. This new variety resembles its seed parent in that its leaves are more or less the same in color and shape. It differs therefrom in that its leaves and flowers are larger while its flowers are less blue and more scarlet in flower color and more fringed. My azalea is distinguishable mainly by its scarlet red color, which is truly different, by its profuse blooming and ease of forcing and by its rapid growth with lush green foliage.

(III) The accompanying drawings comprise two photographic color reproductions wherein: one shows one complete plant constituting a typical specimen of my new azalea variety; and the other shows a few adjacent flowers on said plant, this reproduction being centered primarily on two adjacent flowers and being made on a much larger scale to illustrate the flowers in detail.

(IV) This new variety has been asexually reproduced at Louisville, Ky. over the last several years by cuttings. The resulting plants demonstrate that this new variety holds its distinguishing characteristics through succeeding propagations by cuttings.

*Plants*

(V) The plants grown and observed in Louisville, Ky. stand 12 to 15" high when 2 to 3 years old and, having been observed over a 2 to 3 year period, appear to be reasonably resistant to disease and to winter kill under moderate winter (12–32° F.) conditions. They are of compact, well and uniformly branched growth, neither dense nor sparse, with rigid woody stems of average length and large thickness. The plants are good for forcing and bloom profusely indoors from late December to late April. They have excellent keeping and shipping qualities.

*Foliage*

(VI) The established leaves are similar to but larger than the Kurume azalea and the Hexe. They have an elliptic shape, ranging from about 1 to about 1½" in length and from about ¾ to about 1" in width. In color, the established leaves have a waxy, glossy upper-side surface of dark green and an underside surface of light green, while the new leaves have an upper-side surface of light green and an underside surface of a light green.

*Flowers*

(VII) The flowers have a hose-in-hose petal arrangement. Their maximum diameter averages about 2½ inches. They are borne in clusters of from 2 to 4 flowers. They are larger and more fringed than the pollen parent Hexe. By "more fringed" I mean that the serrations of my variety are greater in number, depth and band width than the pollen parent Hexe flower. The inner centrally exposed hose has 5 petals while the outer surrounding hose has 5 petals, which are offset. The petals of both hoses have a comparatively uniform deep scarlet coloring of an exceptionally beautiful red character without the blue characteristic of the Hexe flower. The texture of the flower is heavy and waxy; blooming is uniform. The flowers hold exceptionally well most any time of the year, even in summer during off-season flowering.

(VIII) The stamens are 5 in number and 1" long. The stigma is large (⅛ to 5/32" across) and faces upward, 5 lobed at tip. The style is scarlet red, stout and curved upward. The ovary is red and pubescent. The sepal behind the standard part of the corolla is 1¼" long when in full flower. The sepal behind the wing part of the corolla is 1" long when in full flower. The calyx is 5 lobed and heavily pubescent. The tube is rather short (½") in length and open type. The flower lobes are large, 1¼" long and 1¼" wide and fringed. The inside of the flower is smooth.

*Transmitted and reflected colors*

(IX) On a General Electric Recording Spectrophotometer the petals transmitted and reflected colors as follows:

(A) Transmittance ranged—
- (1) for violet from 7.5% at 400 mu to 8% at 410 to 5.5% at 450,
- (2) for blue from 5.5% at 450 to 1% at 490,
- (3) for green from 1% at 490 to 5% at 560,
- (4) for yellow from 5% at 560 to 17% at 590,
- (5) for orange from 17% at 490 to 32% at 630,
- (6) for red from 32% at 630 to 37.5% at 700, and (B) Reflectance ranged—
- (1) for violet from the 12.5–17.0% range at 400 to 8.5% at 450,
- (2) for blue from 8.5% at 450 to the 4–5% range at 490,
- (3) for green from the 4–5% range at 490 to the 8–12% range at 560,
- (4) for yellow from the 8–12% range at 560 to the 27–33% range at 590,
- (5) for orange from the 27–33% range at 590 to 62–64% range at 630,
- (6) for red from the 62–64% range at 630 to the 79–80% range at 750.

*Cuttings*

(X) The cuttings root easily and reproduce true to form.

(XI) In addition to the desired improvements heretofore unknown in azaleas of this type, several other unique and distinguishing characteristics exist. My new variety of azalea differs from the pollen parent "Hexe" in that my variety has larger flowers, the color of which is rich scarlet red, while that of the pollen parent is bluish-red. In comparison with the seed parent "#1960–1," the same pronounced improvement in color is apparent. The increased size of the flower when compared with #1960–1 is also pronounced, the individual flowers of my variety being approximately twice the size of those of #1960–1 single red. While there is a marked similarity in plant habit between my new variety and "Hexe," the rate of growth of my variety is approximately twice that of "Hexe." The intensity of rich scarlet red color in combination with the durability of the flower and its ability to remain on the plant for an unusually long time makes this variety truly outstanding.

(XII) These characteristics have all been proven consistent and stable during many successive generations of asexually produced plants which have been propagated by me from cuttings at Louisville, Ky.

*Horticultural description*

(XIII) Semi-evergreen, small shrub of the florists' forcing type, of dense growth, producing a profusion of rich flowers of scarlet red. The foliage is abundant, dark green, very shiny on the upper surface, and light green on the lower surface. The leaves are medium sized, 1 to 1½" long, and ¾ to 1" in width, elliptic shaped. The young foliage is light green above and below, usually somewhat lighter on the lower surface. The terminal flowering buds are pointed and enclosed in several scales. The flowering buds are large and pointed. Each influorescence bears from 2–4 flowers. The bud color is scarlet.

(XIV) The flower is of the hose-in-hose type. The outer hose is perfect. The mature flower is about 1¾ inches deep and 2½ inches across. The flower is of the formal type, broad, but with fringed edges. The color is scarlet red with very little change in color as the flower ages. The flower is retained on the plant for 7–10 days after fully open. The stamens are normally 5, scarlet red, slender and gracefully curved. The style is about as long as the flower, scarlet red, slender and curved.

(XV) The variety can be forced for Christmas, but is best when forced in the early spring. Natural blooming period is late December to late April in Louisville, Ky. The variety is extremely fast growing and cuttings strike readily. Growth on its own roots is sufficiently rapid to enable the production of finished plants with heads 6 to 8 inches in diameter in two years. This variety is readily adaptable to the new technique of blooming off season with the growth retardants on the market today. Its good response to this retardant treatment makes it possible to set bud for year round azaleas.

(XVI) Having disclosed my invention in the above descriptions and in the accompanying photos, what I claim as new and patentable is:

A distinct variety of azalea of the florists' forcing type as shown and described, mainly distinguishable by its scarlet red color which is truly different, by its rapid growth and lush green foliage, by its profuse blooming and ease of forcing and by its dependability to set bud under the growth retardant conditions required for year round azaleas.

No references cited.

ABRAHAM G. STONE, *Primary Examiner.*

ROBERT E. BAGWILL, *Examiner.*